United States Patent

(12) United States Patent
Rice et al.

(10) Patent No.: US 6,326,164 B1
(45) Date of Patent: Dec. 4, 2001

(54) METHODS FOR DETERMINING DEOXYXYLULOSE 5-PHOSPHATE SYNTHASE ACTIVITY

(75) Inventors: John W. Rice, Pittsboro; Andreas S. Kloti, Durham; John M. Crawford, Jr., Raleigh; Beth Lanning, Cary; Sandy J. Stewart, Durham, all of NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/626,589

(22) Filed: Jul. 27, 2000

(51) Int. Cl.[7] ............................... C12Q 1/26; C12N 9/02
(52) U.S. Cl. ............................................. 435/25; 435/189
(58) Field of Search .......................... 435/25, 26

(56) References Cited

FOREIGN PATENT DOCUMENTS

98/33936 * 2/1998 (WO) .
00/08169 * 2/2000 (WO) .

OTHER PUBLICATIONS

Moran et al. "A rapid beta–NADH–linked fluorescence assay for lactate dehydrogenase in cellular death" (1996) J Pharmacol Toxicol Methods, 36:41–44.*

Singh et al. "A high performance liquid chromatography assay for threonine/serine dehydratase" (1992) Anal Biochem, 208:260–263.*

Eisenreich, W. et al., "The deoxyxylulose phosphate pathway of terpenoid biosynthesis in plants and microorganisms," Chemistry & Biology, Current Biology Publications (Germany), p. R221–R223, (Sep., 1998).

Lange, B. M. et al., "A family of transketolases that directs isoprenoid biosynthesis via a mevalonate–independent pathway," Proc. Natl. Sci. USA, The National Academy of Sciences (US), pp. 2100–2104, (Mar. 1998).

Lois, L. M. et al., "Cloning and characterization of a gene from *Escherichia coli* encoding a transketolase–like enzyme that catalyzes the synthesis of D–1–deoxyxylulose 5–phosphate, a common precursor for isoprenoid, thiamin, and pyridoxol biosynthesis," Proc. Natl. Acad. Sci. USA, The National Acadamy of Sciences (US), pp. 2105–2110, (Mar. 1998).

Sprenger, G. et al., "Identification of a thiamin–dependent synthase in *Escherichia coli* required for the formation of the 1–deoxy–D–xylulose 5–phosphate precursor to isoprenoids, thiamin, and pyridoxol," Proc. Natl. Acad. Sci. USA, The National Acadamy of Sciences (USA), pp. 12857–12862, (Nov., 1997).

* cited by examiner

Primary Examiner—Rebecca E. Prouty
Assistant Examiner—David Steadman
(74) Attorney, Agent, or Firm—Elaine T. Sale; Joseph T. Majka; Henry Nowak

(57) ABSTRACT

The invention is directed to methods and compositions for the determination of deoxyxylulose 5-phosphate synthase (DXPS) activity. The methods and compositions of the invention are amenable to high-throughput screening assays for the identification of inhibitors and enhancers of DXPS activity. Such compounds have use in the modulation of plant and microbial growth. The compositions of the invention are DXPS fragments and chimeric polypeptides that have increased solubility as compared to the wild-type DXPS polypeptide. These DXPS fragments and chimeric polypeptides can be recombinantly expressed and purified in quantities suitable for high-throughput screening assays. The assays of the invention are based on the detection of substrates of DXPS that remain after a DXPS reaction.

17 Claims, 10 Drawing Sheets

Figure 2

| Trx | His-tag | thrombin | S-tag | EK | tDXPS |

SEQUENCE LISTING

```
<160> NUMBER OF SEQ ID NOS:  6

<210> SEQ ID NO 1
<211> LENGTH: 717
<212> TYPE: PRT
<213> ORGANISM: Arabidopsis thaliana

<400> SEQUENCE: 1

Met Ala Ser Ser Ala Phe Ala Phe Pro Ser Tyr Ile Ile Thr Lys Gly
 1               5                   10                  15

Gly Leu Ser Thr Asp Ser Cys Lys Ser Thr Ser Leu Ser Ser Ser Arg
                20                  25                  30

Ser Leu Val Thr Asp Leu Pro Ser Pro Cys Leu Lys Pro Asn Asn Asn
            35                  40                  45

Ser His Ser Asn Arg Arg Ala Lys Val Cys Ala Ser Leu Ala Glu Lys
        50                  55                  60

Gly Glu Tyr Tyr Ser Asn Arg Pro Pro Thr Pro Leu Leu Asp Thr Ile
```

-continued

```
 65                  70                  75                  80
Asn Tyr Pro Ile His Met Lys Asn Leu Ser Val Lys Glu Leu Lys Gln
                85                  90                  95
Leu Ser Asp Glu Leu Arg Ser Asp Val Ile Phe Asn Val Ser Lys Thr
                100                 105                 110
Gly Gly His Leu Gly Ser Ser Leu Gly Val Val Glu Leu Thr Val Ala
                115                 120                 125
Leu His Tyr Ile Phe Asn Thr Pro Gln Asp Lys Ile Leu Trp Asp Val
                130                 135                 140
Gly His Gln Ser Tyr Pro His Lys Ile Leu Thr Gly Arg Arg Gly Lys
145                 150                 155                 160
Met Pro Thr Met Arg Gln Thr Asn Gly Leu Ser Gly Phe Thr Lys Arg
                165                 170                 175
Gly Glu Ser Glu His Asp Cys Phe Gly Thr Gly His Ser Ser Thr Thr
                180                 185                 190
Ile Ser Ala Gly Leu Gly Met Ala Val Gly Arg Asp Leu Lys Gly Lys
                195                 200                 205
Asn Asn Asn Val Val Ala Val Ile Gly Asp Gly Ala Met Thr Ala Gly
    210                 215                 220
Gln Ala Tyr Glu Ala Met Asn Asn Ala Gly Tyr Leu Asp Ser Asp Met
225                 230                 235                 240
Ile Val Ile Leu Asn Asp Asn Lys Gln Val Ser Leu Pro Thr Ala Thr
                245                 250                 255
Leu Asp Gly Pro Ser Pro Pro Val Gly Ala Leu Ser Ser Ala Leu Ser
                260                 265                 270
Arg Leu Gln Ser Asn Pro Ala Leu Arg Glu Leu Arg Glu Val Ala Lys
                275                 280                 285
Gly Met Thr Lys Gln Ile Gly Gly Pro Met His Gln Leu Ala Ala Lys
                290                 295                 300
Val Asp Glu Tyr Ala Arg Gly Met Ile Ser Gly Thr Gly Ser Ser Leu
305                 310                 315                 320
Phe Glu Glu Leu Gly Leu Tyr Tyr Ile Gly Pro Val Asp Gly His Asn
                325                 330                 335
Ile Asp Asp Leu Val Ala Ile Leu Lys Glu Val Lys Ser Thr Arg Thr
                340                 345                 350
Thr Gly Pro Val Leu Ile His Val Val Thr Glu Lys Gly Arg Gly Tyr
                355                 360                 365
Pro Tyr Ala Glu Arg Ala Asp Asp Lys Tyr His Gly Val Val Lys Phe
370                 375                 380
Asp Pro Ala Thr Gly Arg Gln Phe Lys Thr Thr Asn Lys Thr Gln Ser
385                 390                 395                 400
Tyr Thr Thr Tyr Phe Ala Glu Ala Leu Val Ala Glu Ala Glu Val Asp
                405                 410                 415
Lys Asp Val Val Ala Ile His Ala Ala Met Gly Gly Gly Thr Gly Leu
                420                 425                 430
Asn Leu Phe Gln Arg Arg Phe Pro Thr Arg Cys Phe Asp Val Gly Ile
                435                 440                 445
Ala Glu Gln His Ala Val Thr Phe Ala Ala Gly Leu Ala Cys Glu Gly
                450                 455                 460
Leu Lys Pro Phe Cys Ala Ile Tyr Ser Ser Phe Met Gln Arg Ala Tyr
465                 470                 475                 480
Asp Gln Val Val His Asp Val Asp Leu Gln Lys Leu Pro Val Arg Phe
                485                 490                 495
```

```
Ala Met Asp Arg Ala Gly Leu Val Gly Ala Asp Gly Pro Thr His Cys
            500                 505                 510

Gly Ala Phe Asp Val Thr Phe Met Ala Cys Leu Pro Asn Met Ile Val
            515                 520                 525

Met Ala Pro Ser Asp Glu Ala Asp Leu Phe Asn Met Val Ala Thr Ala
            530                 535                 540

Val Ala Ile Asp Asp Arg Pro Ser Cys Phe Arg Tyr Pro Arg Gly Asn
545                 550                 555                 560

Gly Ile Gly Val Ala Leu Pro Pro Gly Asn Lys Gly Val Pro Ile Glu
            565                 570                 575

Ile Gly Lys Gly Arg Ile Leu Lys Glu Gly Glu Arg Val Ala Leu Leu
            580                 585                 590

Gly Tyr Gly Ser Ala Val Gln Ser Cys Leu Gly Ala Ala Val Met Leu
            595                 600                 605

Glu Glu Arg Gly Leu Asn Val Thr Val Ala Asp Ala Arg Phe Cys Lys
            610                 615                 620

Pro Leu Asp Arg Ala Leu Ile Arg Ser Leu Ala Lys Ser His Glu Val
625                 630                 635                 640

Leu Ile Thr Val Glu Glu Gly Ser Ile Gly Gly Phe Gly Ser His Val
            645                 650                 655

Val Gln Phe Leu Ala Leu Asp Gly Leu Leu Asp Gly Lys Leu Lys Trp
            660                 665                 670

Arg Pro Met Val Leu Pro Asp Arg Tyr Ile Asp His Gly Ala Pro Ala
            675                 680                 685

Asp Gln Leu Ala Glu Ala Gly Leu Met Pro Ser His Ile Ala Ala Thr
            690                 695                 700

Ala Leu Asn Leu Ile Gly Ala Pro Arg Glu Ala Leu Phe
705                 710                 715

<210> SEQ ID NO 2
<211> LENGTH: 659
<212> TYPE: PRT
<213> ORGANISM: Arabidopsis thaliana

<400> SEQUENCE: 2

Ala Ser Leu Ala Glu Lys Gly Glu Tyr Tyr Ser Asn Arg Pro Pro Thr
1               5                   10                  15

Pro Leu Leu Asp Thr Ile Asn Tyr Pro Ile His Met Lys Asn Leu Ser
            20                  25                  30

Val Lys Glu Leu Lys Gln Leu Ser Asp Glu Leu Arg Ser Asp Val Ile
            35                  40                  45

Phe Asn Val Ser Lys Thr Gly Gly His Leu Gly Ser Ser Leu Gly Val
            50                  55                  60

Val Glu Leu Thr Val Ala Leu His Tyr Ile Phe Asn Thr Pro Gln Asp
65                  70                  75                  80

Lys Ile Leu Trp Asp Val Gly His Gln Ser Tyr Pro His Lys Ile Leu
            85                  90                  95

Thr Gly Arg Arg Gly Lys Met Pro Thr Met Arg Gln Thr Asn Gly Leu
            100                 105                 110

Ser Gly Phe Thr Lys Arg Gly Glu Ser Glu His Asp Cys Phe Gly Thr
            115                 120                 125

Gly His Ser Ser Thr Thr Ile Ser Ala Gly Leu Gly Met Ala Val Gly
            130                 135                 140

Arg Asp Leu Lys Gly Lys Asn Asn Asn Val Val Ala Val Ile Gly Asp
```

```
145                 150                 155                 160
Gly Ala Met Thr Ala Gly Gln Ala Tyr Glu Ala Met Asn Asn Ala Gly
                165                 170                 175
Tyr Leu Asp Ser Asp Met Ile Val Ile Leu Asn Asp Asn Lys Gln Val
            180                 185                 190
Ser Leu Pro Thr Ala Thr Leu Asp Gly Pro Ser Pro Val Gly Ala
            195                 200                 205
Leu Ser Ser Ala Leu Ser Arg Leu Gln Ser Asn Pro Ala Leu Arg Glu
            210                 215                 220
Leu Arg Glu Val Ala Lys Gly Met Thr Lys Gln Ile Gly Gly Pro Met
225                 230                 235                 240
His Gln Leu Ala Ala Lys Val Asp Glu Tyr Ala Arg Gly Met Ile Ser
                245                 250                 255
Gly Thr Gly Ser Ser Leu Phe Glu Glu Leu Gly Leu Tyr Tyr Ile Gly
            260                 265                 270
Pro Val Asp Gly His Asn Ile Asp Asp Leu Val Ala Ile Leu Lys Glu
        275                 280                 285
Val Lys Ser Thr Arg Thr Gly Pro Val Leu Ile His Val Val Thr
    290                 295                 300
Glu Lys Gly Arg Gly Tyr Pro Tyr Ala Glu Arg Ala Asp Asp Lys Tyr
305                 310                 315                 320
His Gly Val Val Lys Phe Asp Pro Ala Thr Gly Arg Gln Phe Lys Thr
                325                 330                 335
Thr Asn Lys Thr Gln Ser Tyr Thr Thr Tyr Phe Ala Glu Ala Leu Val
            340                 345                 350
Ala Glu Ala Glu Val Asp Lys Asp Val Val Ala Ile His Ala Ala Met
            355                 360                 365
Gly Gly Gly Thr Gly Leu Asn Leu Phe Gln Arg Arg Phe Pro Thr Arg
    370                 375                 380
Cys Phe Asp Val Gly Ile Ala Glu Gln His Ala Val Thr Phe Ala Ala
385                 390                 395                 400
Gly Leu Ala Cys Glu Gly Leu Lys Pro Phe Cys Ala Ile Tyr Ser Ser
                405                 410                 415
Phe Met Gln Arg Ala Tyr Asp Gln Val Val His Asp Val Asp Leu Gln
            420                 425                 430
Lys Leu Pro Val Arg Phe Ala Met Asp Arg Ala Gly Leu Val Gly Ala
            435                 440                 445
Asp Gly Pro Thr His Cys Gly Ala Phe Asp Val Thr Phe Met Ala Cys
    450                 455                 460
Leu Pro Asn Met Ile Val Met Ala Pro Ser Asp Glu Ala Asp Leu Phe
465                 470                 475                 480
Asn Met Val Ala Thr Ala Val Ala Ile Asp Asp Arg Pro Ser Cys Phe
                485                 490                 495
Arg Tyr Pro Arg Gly Asn Gly Ile Gly Val Ala Leu Pro Pro Gly Asn
            500                 505                 510
Lys Gly Val Pro Ile Glu Ile Gly Lys Gly Arg Ile Leu Lys Glu Gly
        515                 520                 525
Glu Arg Val Ala Leu Leu Gly Tyr Gly Ser Ala Val Gln Ser Cys Leu
    530                 535                 540
Gly Ala Ala Val Met Leu Glu Glu Arg Gly Leu Asn Val Thr Val Ala
545                 550                 555                 560
Asp Ala Arg Phe Cys Lys Pro Leu Asp Arg Ala Leu Ile Arg Ser Leu
                565                 570                 575
```

```
Ala Lys Ser His Glu Val Leu Ile Thr Val Glu Glu Gly Ser Ile Gly
            580                 585                 590

Gly Phe Gly Ser His Val Val Gln Phe Leu Ala Leu Asp Gly Leu Leu
            595                 600                 605

Asp Gly Lys Leu Lys Trp Arg Pro Met Val Leu Pro Asp Arg Tyr Ile
            610                 615                 620

Asp His Gly Ala Pro Ala Asp Gln Leu Ala Glu Ala Gly Leu Met Pro
625                 630                 635                 640

Ser His Ile Ala Ala Thr Ala Leu Asn Leu Ile Gly Ala Pro Arg Glu
                645                 650                 655

Ala Leu Phe

<210> SEQ ID NO 3
<211> LENGTH: 824
<212> TYPE: PRT
<213> ORGANISM: Artificial Sequence
<220> FEATURE:
<223> OTHER INFORMATION: Residues 1-165 are from the thioredoxin
      sequence found in the vector pET32 supplied by Novagen.
      Residues 166-824 represent the tDXPS sequence from
      Arabidopsis shown in SEQ ID NO:2.

<400> SEQUENCE: 3

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
            130                 135                 140

His Met Asp Ser Pro Asp Leu Gly Thr Asp Asp Asp Lys Ala Met
145                 150                 155                 160

Ala Asp Ile Gly Ser Ala Ser Leu Ala Glu Lys Gly Glu Tyr Tyr Ser
                165                 170                 175

Asn Arg Pro Pro Thr Pro Leu Leu Asp Thr Ile Asn Tyr Pro Ile His
            180                 185                 190

Met Lys Asn Leu Ser Val Lys Glu Leu Lys Gln Leu Ser Asp Glu Leu
            195                 200                 205

Arg Ser Asp Val Ile Phe Asn Val Ser Lys Thr Gly Gly His Leu Gly
            210                 215                 220

Ser Ser Leu Gly Val Val Glu Leu Thr Val Ala Leu His Tyr Ile Phe
225                 230                 235                 240

Asn Thr Pro Gln Asp Lys Ile Leu Trp Asp Val Gly His Gln Ser Tyr
                245                 250                 255
```

```
Pro His Lys Ile Leu Thr Gly Arg Arg Gly Lys Met Pro Thr Met Arg
         260                 265                 270

Gln Thr Asn Gly Leu Ser Gly Phe Thr Lys Arg Gly Glu Ser Glu His
         275                 280                 285

Asp Cys Phe Gly Thr Gly His Ser Ser Thr Thr Ile Ser Ala Gly Leu
         290                 295                 300

Gly Met Ala Val Gly Arg Asp Leu Lys Gly Lys Asn Asn Asn Val Val
305                 310                 315                 320

Ala Val Ile Gly Asp Gly Ala Met Thr Ala Gly Gln Ala Tyr Glu Ala
                 325                 330                 335

Met Asn Asn Ala Gly Tyr Leu Asp Ser Asp Met Ile Val Ile Leu Asn
         340                 345                 350

Asp Asn Lys Gln Val Ser Leu Pro Thr Ala Thr Leu Asp Gly Pro Ser
         355                 360                 365

Pro Pro Val Gly Ala Leu Ser Ser Ala Leu Ser Arg Leu Gln Ser Asn
         370                 375                 380

Pro Ala Leu Arg Glu Leu Arg Glu Val Ala Lys Gly Met Thr Lys Gln
385                 390                 395                 400

Ile Gly Gly Pro Met His Gln Leu Ala Ala Lys Val Asp Glu Tyr Ala
                 405                 410                 415

Arg Gly Met Ile Ser Gly Thr Gly Ser Ser Leu Phe Glu Glu Leu Gly
         420                 425                 430

Leu Tyr Tyr Ile Gly Pro Val Asp Gly His Asn Ile Asp Asp Leu Val
         435                 440                 445

Ala Ile Leu Lys Glu Val Lys Ser Thr Arg Thr Thr Gly Pro Val Leu
         450                 455                 460

Ile His Val Val Thr Glu Lys Gly Arg Gly Tyr Pro Tyr Ala Glu Arg
465                 470                 475                 480

Ala Asp Asp Lys Tyr His Gly Val Val Lys Phe Asp Pro Ala Thr Gly
                 485                 490                 495

Arg Gln Phe Lys Thr Thr Asn Lys Thr Gln Ser Tyr Thr Thr Tyr Phe
         500                 505                 510

Ala Glu Ala Leu Val Ala Glu Ala Glu Val Asp Lys Asp Val Val Ala
         515                 520                 525

Ile His Ala Ala Met Gly Gly Gly Thr Gly Leu Asn Leu Phe Gln Arg
         530                 535                 540

Arg Phe Pro Thr Arg Cys Phe Asp Val Gly Ile Ala Glu Gln His Ala
545                 550                 555                 560

Val Thr Phe Ala Ala Gly Leu Ala Cys Glu Gly Leu Lys Pro Phe Cys
                 565                 570                 575

Ala Ile Tyr Ser Ser Phe Met Gln Arg Ala Tyr Asp Gln Val Val His
         580                 585                 590

Asp Val Asp Leu Gln Lys Leu Pro Val Arg Phe Ala Met Asp Arg Ala
         595                 600                 605

Gly Leu Val Gly Ala Asp Gly Pro Thr His Cys Gly Ala Phe Asp Val
         610                 615                 620

Thr Phe Met Ala Cys Leu Pro Asn Met Ile Val Met Ala Pro Ser Asp
625                 630                 635                 640

Glu Ala Asp Leu Phe Asn Met Val Ala Thr Ala Val Ala Ile Asp Asp
                 645                 650                 655

Arg Pro Ser Cys Phe Arg Tyr Pro Arg Gly Asn Gly Ile Gly Val Ala
         660                 665                 670

Leu Pro Pro Gly Asn Lys Gly Val Pro Ile Glu Ile Gly Lys Gly Arg
```

675                 680                 685
    Ile Leu Lys Glu Gly Glu Arg Val Ala Leu Leu Gly Tyr Gly Ser Ala
                690                 695                 700

Val Gln Ser Cys Leu Gly Ala Ala Val Met Leu Glu Glu Arg Gly Leu
    705                 710                 715                 720

Asn Val Thr Val Ala Asp Ala Arg Phe Cys Lys Pro Leu Asp Arg Ala
                    725                 730                 735

Leu Ile Arg Ser Leu Ala Lys Ser His Glu Val Leu Ile Thr Val Glu
                740                 745                 750

Glu Gly Ser Ile Gly Gly Phe Gly Ser His Val Val Gln Phe Leu Ala
                    755                 760                 765

Leu Asp Gly Leu Leu Asp Gly Lys Leu Lys Trp Arg Pro Met Val Leu
                770                 775                 780

Pro Asp Arg Tyr Ile Asp His Gly Ala Pro Ala Asp Gln Leu Ala Glu
    785                 790                 795                 800

Ala Gly Leu Met Pro Ser His Ile Ala Ala Thr Ala Leu Asn Leu Ile
                    805                 810                 815

Gly Ala Pro Arg Glu Ala Leu Phe
                820

<210> SEQ ID NO 4
<211> LENGTH: 2151
<212> TYPE: DNA
<213> ORGANISM: Arabidopsis thaliana

<400> SEQUENCE: 4
atggcttctt ctgcatttgc ttttccttct tacataataa ccaaaggagg actttcaact    60
gattcttgta aatcaacttc tttgtcttct tctagatctt tggttacaga tcttccatca   120
ccatgtctga aacccaacaa caattcccat tcaaacagaa gagcaaaagt gtgtgcttca   180
cttgcagaga agggtgaata ttattcaaac agaccaccaa ctccattact tgacactatt   240
aactacccaa tccacatgaa aaatctttct gtcaaggaac tgaaacaact ttctgatgag   300
ctgagatcag acgtgatctt aatgtgtcg aaaaccggtg acatttggg tcaagtctt    360 ggtgttgtgg agcttactgt ggctcttcat tacattttca atactccaca agacaagatt   420
ctttgggatg ttggtcatca gtcttatcct cataagattc ttactgggag aagaggaaag   480
atgcctacaa tgaggcaaac caatggtctc tctggtttca ccaaacgagg agagagtgaa   540
catgattgct ttggtactgg acacagctca accacaatat ctgctggttt aggaatggcg   600
gtaggaaggg atttgaaggg gaagaacaac aatgtggttg ctgtgattgg tgatggtgcg   660
atgacggcag gacaggctta tgaagccatg aacaacgccg gatatctaga ctctgatatg   720
attgtgattc ttaatgacaa caagcaagtc tcattaccta cagctacttt ggatggacca   780
agtccacctg ttggtgcatt gagcagtgct cttagtcggt acagtctaa cccggctctc   840 agagagttga gaagtcgc aaagggtatg acaaagcaaa taggcggacc aatgcatcag   900
ttggcggcta agtagatga gtatgctcga ggaatgataa gcgggactgg atcgtcactg   960
tttgaagaac tcggtcttta ctatattggt ccagttgatg gcacaacat agatgatttg  1020 gtagccattc ttaaagaagt taagagtacc agaaccacag acctgtact tattcatgtg  1080 gtgacggaga aggtcgtgg ttatccttac gcggagagag ctgatgacaa ataccatggt  1140
gttgtgaaat tgatccagc aacgggtaga cagttcaaaa ctactaataa gactcaatct  1200
tacacaactt actttgcgga ggcattagtc gcagaagcag aggtagacaa agatgtggtt  1260

-continued

```
gcgattcatg cagccatggg aggtggaacc gggttaaatc tctttcaacg tcgcttccca   1320
acaagatgtt tcgatgtagg aatagcggaa caacacgcag ttacttttgc tgcgggttta   1380
gcctgtgaag gccttaaacc cttctgtgca atctattcgt ctttcatgca gcgtgcttat   1440
gaccaggttg tccatgatgt tgatttgcaa aaattaccgg tgagatttgc aatggataga   1500
gctggactcg ttggagctga tggtccgaca cattgtggag ctttcgatgt gacatttatg   1560
gcttgtcttc ctaacatgat agtgatggct ccatcagatg aagcagatct ctttaacatg   1620
gttgcaactg ctgttgcgat tgatgatcgt ccttcttgtt tccgttaccc tagaggtaac   1680
ggtattggag ttgcattacc tcccggaaac aaaggtgttc aattgagat  tgggaaaggt   1740 agaattttaa aggaaggaga gagagttgcg ttgttgggtt atggctcagc agttcagagc   1800
tgtttaggag cggctgtaat gctcgaagaa cgcggattaa acgtaactgt agcggatgca   1860
cggttttgca agccattgga ccgtgctctc attcgcagct tagctaagtc gcacgaggtt   1920
ctgatcacgg ttgaagaagg ttccattgga ggttttggct cgcacgttgt tcagtttctt   1980
gctctcgatg gtcttcttga tggcaaactc aagtggagac caatggtact gcctgatcga   2040
tacattgatc acggtgcacc agctgatcaa ctagctgaag ctggactcat gccatctcac   2100
atcgcagcaa ccgcacttaa cttaatcggt gcaccaaggg aagctctgtt t            2151

<210> SEQ ID NO 5
<211> LENGTH: 1977
<212> TYPE: DNA
<213> ORGANISM: Arabiodopsis thaliana

<400> SEQUENCE: 5
gcttcacttg cagagaaggg tgaatatat  tcaaacagac caccaactcc attacttgac     60
actattaact acccaatcca catgaaaaat ctttctgtca aggaactgaa acaactttct    120
gatgagctga gatcagacgt gatctttaat gtgtcgaaaa ccggtggaca tttggggtca    180
agtcttggtg ttgtggagct tactgtggct cttcattaca ttttcaatac tccacaagac    240
aagattcttt gggatgttgg tcatcagtct tatcctcata agattcttac tgggagaaga    300
ggaaagatgc ctacaatgag gcaaaccaat ggtctctctg gtttccaccaa acgaggagag   360 agtgaacatg attgctttgg tactggacac agctcaacca caatatctgc tggtttagga    420
atggcggtag gaagggattt gaaggggaag aacaacaatg tggttgctgt gattggtgat    480
ggtgcgatga cggcaggaca ggcttatgaa gccatgaaca acgccggata tctagactct    540
gatatgattg tgattcttaa tgacaacaag caagtctcat tacctacagc tactttggat    600
ggaccaagtc cacctgttgg tgcattgagc agtgctctta gtcggttaca gtctaacccg    660
gctctcagag agttgagaga agtcgcaaag ggtatgacaa agcaaatagg cggaccaatg    720
catcagttgg cggctaaggt agatgagtat gctcgaggaa tgataagcgg gactggatcg    780
tcactgtttg aagaactcgg tctttactat attggtccag ttgatgggca acatagat     840 gatttggtag ccattcttaa agaagttaag agtaccagaa ccacaggacc tgtacttatt    900
catgtggtga cggagaaagg tcgtggttat ccttacgcgg agagagctga tgacaaatac    960
catggtgttg tgaaatttga tccagcaacg ggtagacagt tcaaaactac taataagact   1020
caatcttaca caacttactt tgcggaggca ttagtcgcag aagcagaggt agacaaagat   1080
gtggttgcga ttcatgcagc catgggaggt ggaaccgggt taaatctctt caacgtcgc   1140 ttcccaacaa gatgtttcga tgtaggaata gcggaacaac acgcagttac ttttgctgcg   1200
ggtttagcct gtgaaggcct taaacccttc tgtgcaatct attcgtcttt catgcagcgt   1260
```

```
gcttatgacc aggttgtcca tgatgttgat ttgcaaaaat taccggtgag atttgcaatg   1320
gatagagctg gactcgttgg agctgatggt ccgacacatt gtggagcttt cgatgtgaca   1380
tttatggctt gtcttcctaa catgatagtg atggctccat cagatgaagc agatctcttt   1440
aacatggttg caactgctgt tgcgattgat gatcgtcctt cttgtttccg ttaccctaga   1500
ggtaacggta ttggagttgc attacctccc ggaaacaaag gtgttccaat tgagattggg   1560
aaaggtagaa ttttaaagga aggagagaga gttgcgttgt tgggttatgg ctcagcagtt   1620
cagagctgtt taggagcggc tgtaatgctc gaagaacgcg gattaaacgt aactgtagcg   1680
gatgcacggt tttgcaagcc attggaccgt gctctcattc gcagcttagc taagtcgcac   1740
gaggttctga tcacggttga agaaggttcc attggaggtt ttggctcgca cgttgttcag   1800
tttcttgctc tcgatggtct tcttgatggc aaactcaagt ggagaccaat ggtactgcct   1860
gatcgataca ttgatcacgg tgcaccagct gatcaactag ctgaagctgg actcatgcca   1920
tctcacatcg cagcaaccgc acttaactta atcggtgcac aagggaagc tctgttt      1977
```

<210> SEQ ID NO 6
<211> LENGTH: 2472
<212> TYPE: DNA
<213> ORGANISM: Artificial Sequence
<220> FEATURE:
<223> OTHER INFORMATION: Nucleotides 1-495 encode the thioredoxin
      sequence found in the vector pET32 supplied by Novagen.
      Nucleotides 496-2472 represent the tDXPS cDNA
      sequence from Arabidopsis thaliana.

<400> SEQUENCE: 6

```
atgagcgata aaattattca cctgactgac gacagttttg cacggatgt actcaaagcg     60 gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatatgca ccatcatcat    360
catcattctt ctggtctggt gccacgcggt tctggtatga agaaaccgc tgctgctaaa    420 ttcgaacgcc agcacatgga cagcccagat ctgggtaccg acgacgacga caaggccatg    480
gctgatatcg atccgcttc acttgcagag aagggtgaat attattcaaa cagaccacca    540
actccattac ttgacactat taactaccca atccacatga aaaatctttc tgtcaaggaa    600
ctgaaacaac tttctgatga gctgagatca gacgtgatct ttaatgtgtc gaaaaccggt    660
ggacatttgg ggtcaagtct tggtgttgtg agcttactg tggctcttca ttacattttc    720
aatactccac aagacaagat tctttgggat gttggtcatc agtcttatcc tcataagatt    780
cttactggga gaagaggaaa gatgcctaca atgaggcaaa ccaatggtct ctctggtttc    840
accaaacgag agagagtga acatgattgc tttggtactg acacagctc aaccacaata     900 tctgctggtt taggaatggc ggtaggaagg gattttgaagg ggaagaacaa caatgtggtt    960
gctgtgattg tgatggtgc gatgacggca ggacaggctt atgaagccat gaacaacgcc   1020
ggatatctag actctgatat gattgtgatt cttaatgaca caagcaagt ctcattacct   1080 acagctactt tggatggacc aagtccacct gttggtgcat tgagcagtgc tcttagtcgg   1140
ttacagtcta acccggctct cagagagttg agagaagtcg caagggtat gacaaagcaa   1200 ataggcggac caatgcatca gttggcggct aaggtagatg agtatgctcg aggaatgata   1260
```

```
agcgggactg gatcgtcact gtttgaagaa ctcggtcttt actatattgg tccagttgat    1320
gggcacaaca tagatgattt ggtagccatt cttaaagaag ttaagagtac cagaaccaca    1380
ggacctgtac ttattcatgt ggtgacggag aaaggtcgtg gttatcctta cgcggagaga    1440
gctgatgaca ataccatgg tgttgtgaaa tttgatccag caacgggtag acagttcaaa     1500
actactaata agactcaatc ttacacaact tactttgcgg aggcattagt cgcagaagca    1560
gaggtagaca aagatgtggt tgcgattcat gcagccatgg gaggtggaac cgggttaaat    1620
ctctttcaac gtcgcttccc aacaagatgt ttcgatgtag gaatagcgga acaacacgca    1680
gttacttttg ctgcgggttt agcctgtgaa ggccttaaac ccttctgtgc aatctattcg    1740
tctttcatgc agcgtgctta tgaccaggtt gtccatgatg ttgatttgca aaaattaccg    1800
gtgagatttg caatggatag agctggactc gttggagctg atggtccgac acattgtgga    1860
gctttcgatg tgacatttat ggcttgtctt cctaacatga tagtgatggc tccatcagat    1920
gaagcagatc tctttaacat ggttgcaact gctgttgcga ttgatgatcg tccttcttgt    1980
ttccgttacc ctagaggtaa cggtattgga gttgcattac ctcccggaaa caaaggtgtt    2040
ccaattgaga ttgggaaagg tagaatttta aaggaaggag agagagttgc gttgttgggt    2100
tatggctcag cagttcagag ctgtttagga gcggctgtaa tgctcgaaga acgcggatta    2160
aacgtaactg tagcggatgc acggttttgc aagccattgg accgtgctct cattcgcagc    2220
ttagctaagt cgcacgaggt tctgatcacg gttgaagaag gttccattgg aggttttggc    2280
tcgcacgttg ttcagtttct tgctctcgat ggtcttcttg atggcaaact caagtggaga    2340
ccaatggtac tgcctgatcg atacattgat cacggtgcac cagctgatca actagctgaa    2400
gctggactca tgccatctca catcgcagca accgcactta acttaatcgg tgcaccaagg    2460
gaagctctgt tt                                                        2472
```

METHODS FOR DETERMINING DEOXYXYLULOSE 5-PHOSPHATE SYNTHASE ACTIVITY

FIELD OF THE INVENTION

The present invention relates to assays for measuring deoxyxylulose 5-phosphate synthase (DXPS) activity. The assays can be used to identify compounds that inhibit or enhance DXPS activity. Such compounds have use in modulating plant and microbial growth and development.

BACKGROUND OF THE INVENTION

Deoxy-D-xylulose 5-phosphate (DXP) is a common precursor of thiamin (vitamin B1), pyridoxyl (vitamin B6) and isoprenoids. Isoprenoids encompass a large family of biomolecules, including vitamins A, D, E and K, cholesterol, plant pigments such as carotenoids and the phytol chain of chlorophyll, natural rubber, many essential oils, plant hormones (gibererellins, abscisic acid), insect juvenile hormone, dolichols, quinone electron carriers in mitochondria and chloroplasts, such as ubiquinone and plastoquinone, structural components of membranes (phytosterols) and Ras protein. In higher plants and bacteria, the first step in the formation of isopentenyl diphosphate, the common precursor of all isoprenoids, by the mevalonate-independent pathway is the formation of DXP from the precursors pyruvate and glyceraldehyde 3-phosphate (FIG. 1). The reaction is catalyzed by the enzyme deoxyxylulose 5-phosphate synthase (DXPS) (Lange et al. (1998) *Proc Natl Acad Sci* 95:2100–2104; Lois et. al. (1998) *Proc Natl Acad Sci* 95:2105–2110; Sprenger et al. (1997) *Proc Natl Acad Sci* 94:12857–12862).

The DXPS genes or cDNAs from *E. coli* (GenBank AF035440), *Hemophilus influenzae* (Swiss-Prot P54205), *Rhodobacter capsulatus* (Swiss-Prot P26242), *Synechocystus* sp. PCC6803 (GenBank D90903), *Bacillus subtilis* (Swiss-Prot P54523), *Helicobacter pylori* (GenBank AE000552), *Mycoplasma tuberculosis* (GenBank Z96072), *Glycine max* (GenBank AW278762), *Lycopersicon esculentum* (GenBank AF143812), *Catharanthus roseus* (GenBank AJ011840), *Mentha x peperita* (GenBank AF019383) and *Arabidopsis thaliana* (GenBank AF010383 and 5281015) have been cloned. Also, ESTs encoding fragments of DXPS have been identified in *Oryza sativa, Ricinus communis,* and *Pinus taeda*. However, no homologues of the DXPS genes have been identified in animals.

Disruption of the DXPS gene in Arabidopsis results in an albino phenotype due to a lack of chlorophyll and carotenoid pigments. These results indicate that DXPS is essential for chloroplast function (Lange et al.) and that inhibitors of DXPS activity may have use as herbicides. Accordingly, it would be useful to have a DXPS assay that is amenable to high throughput screening of herbicide candidates.

Several assays for DXPS activity have been reported in the literature. These assays are based on detection of the product, DXP. In these assays, the conversion of $[2-^{14}C]$-pyruvate to $[^{14}C]$-DXP in the presence of glyceraldehyde 3-phosphate and DXPS was measured by detecting $[^{14}C]$-DXP using either reverse phase HPLC (Lange, et. al.) or thin layer chromatography (Lois et al.). However, neither format is suitable for high throughput screening.

SUMMARY OF THE INVENTION

The invention is directed to methods and compositions for the determination of deoxyxylulose 5-phosphate synthase (DXPS) activity. The methods and compositions of the invention are amenable to high throughput screening assays for the identification of inhibitors and enhancers of DXPS activity. Such compounds have use in the modulation of plant growth and development.

The compositions of the invention are DXPS fragments and chimeric polypeptides that have increased solubility in cell extracts as compared to the wild type DXPS polypeptide. These DXPS fragments and chimeric polypeptides can be recombinantly expressed and purified in quantities suitable for high throughput screening assays.

The assays of the invention are based on the detection of substrates of DXPS that remain after a DXPS reaction. Specifically, the invention provides a method for determining deoxyxylulose 5-phosphate synthase activity, comprising:

a) contacting pyruvate and optionally, glyceraldehyde 3-phosphate, with a deoxyxylulose 5-phosphate synthase; and b) determining the concentration of pyruvate and/or glyceraldehyde 3-phosphate remaining after the contact in step (a).

The assays of the invention are useful for the identification of modulators of deoxyxylulose 5-phosphate synthase activity. Thus, in another aspect, the invention provides a method for identifying modulators of deoxyxylulose 5-phosphate synthase activity, comprising:

a) contacting pyruvate and optionally, glyceraldehyde 3-phosphate, with a deoxyxylulose 5-phosphate synthase, in the presence and the absence of at least one candidate modulator; and b) comparing the concentration of pyruvate and/or glyceraldehyde 3-phosphate remaining after said contact in the absence of said candidate modulator to said concentration in the presence of said candidate modulator.

BRIEF DESCRIPTION OF THE DRAWINGS

FIG. 2. Schematic diagram of the trxA/tDXPS chimeric polypeptide.

DETAILED DESCRIPTION

Figure 1:
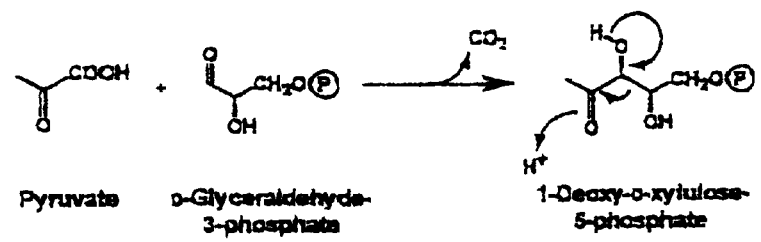
FIG. 1. Schematic diagram showing the conversion of pyruvate and glyceraldehyde 3-phosphate (G 3-P) to deoxyxylulose 5-phosphate (DXP) by deoxyxylulose 5-phosphate synthase (DXPS).
Figure 1:

The present invention discloses methods and compositions for the measurement of the activity of the enzyme deoxyxylulose 5-phosphate synthase (DXPS). In contrast to prior art assays, the assays of the invention are amenable to high throughput screening protocols. Such assays are useful in the rapid identification of inhibitors and enhancers of DXPS activity. Inhibitors of DXPS activity have use as herbicides and as antimicrobial agents. Enhancers of DXPS activity can be used to modulate vitamin B1, vitamin B2 and isoprenoid production in plants and microorganisms.

The compositions of the invention comprise soluble derivatives of *Arabidopsis thaliana* DXPS protein. The full length *Arabidopsis thaliana* DXPS cDNA has previously been reported and is shown in SEQ ID NO:1. However, expression of the full length DXPS protein in baculovirus or *E. coli* expression systems failed to yield soluble protein.

A putative 66 amino acid chloroplast targeting sequence for *A. thaliana* DXPS has been reported in the literature. Sprenger et al. (1997) *Proc Natl Acad Sci* 94:12857–12862. In contrast, we predicted that the targeting sequence corresponded to the N-terminal 58 amino acids of the DXPS protein. The sequence of the truncated *A. thaliana* DXPS protein (tDXPS), from which the N-terminal 58 amino acids have been removed, is shown in SEQ ID NO:2. As discussed below, this truncated protein possesses DXPS activity.

Thus, in one aspect, the invention provides a polypeptide consisting essentially of SEQ ID NO:2. For the purposes of the invention, a polypeptide consisting essentially of SEQ ID NO:2 is limited to the polypeptide of SEQ ID NO:2 and optionally, one to seven additional amino acid residues on the amino and/or carboxy terminus of SEQ ID NO:2.

By "polypeptide" is meant a chain of at least four amino acids joined by peptide bonds. The chain may be linear, branched, circular or combinations thereof. The polypeptides may contain amino acid analogs and other modifications, including, but not limited to glycosylated or phosphorylated residues.

In another aspect, the invention provides a polynucleotide consisting essentially of a nucleic acid encoding the polypeptide of SEQ ID NO:2. In addition, the invention provides an expression cassette comprising an isolated polynucleotide consisting of a nucleic acid encoding the polypeptide of SEQ ID NO:2.

For the purposes of the invention, an "isolated polynucleotide" is a polynucleotide that is substantially free of the nucleic acid sequences that normally flank the polynucleotide in its naturally occurring replicon. For example, a cloned polynucleotide is considered isolated. Alternatively, a polynucleotide is considered isolated if it has been altered by human intervention, or placed in a locus or location that is not its natural site, or if it is introduced into cell by agroinfection.

As used herein, "nucleic acid" and "polynucleotide" refers to RNA or DNA that is linear or branched, single or double stranded, or a hybrid thereof. The term also encompasses RNA/DNA hybrids. Less common bases, such as inosine, 5-methylcytosine, 6-methyladenine, hypoxanthine and others can also be used. Other modifications, such as modifications to the phosphodiester backbone, or the 2-hydroxy in the ribose sugar group of the RNA can also be made.

The polynucleotides of the invention can be inserted into expression cassettes and expression vectors for the production of recombinant DXPS protein. A variety of expression cassettes and vectors are known to those skilled in the art. The expression cassettes of the invention contain 5' and 3' regulatory sequences necessary for transcription and termination of the polynucleotide of interest. Thus, the expression cassettes will include a promoter and a transcriptional terminator. Other functional sequences may be included in the expression cassettes of the invention. Such functional sequences include, but are not limited to, introns, enhancers and translational initiation and termination sites and polyadenylation sites. The control sequences can be those that can function in at least one microorganism, insect cell or plant cell. These sequences may be derived from one or more genes, or can be created using recombinant technology.

Promoters useful in the expression cassettes of the invention include any promoter that is capable of initiating transcription in a microorganism, insect cell or plant cell. The promoter may be constitutive, inducible or tissue-preferred.

Figure 2:
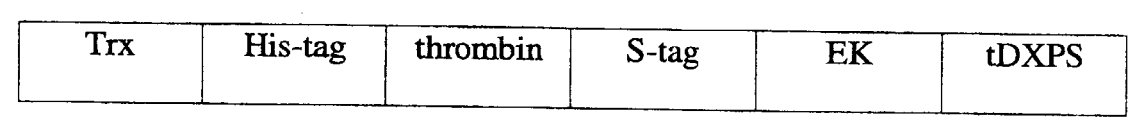

Expression in *E. coli* of tDXPS as a thioredoxin fusion protein (trxA/tDXPS), the sequence of which is shown in SEQ ID NO:3 and diagrammed in FIG. 2, yielded quantities of soluble active protein sufficient for the development of a high throughput screening assay for DXPS activity. Thus, the invention provides a polypeptide comprising SEQ ID NO:3. In addition, the invention provides an isolated polynucleotide comprising a nucleic acid encoding the polypeptide of SEQ ID NO:3.

In another aspect, the invention provides assays for DXPS activity. DXPS catalyzes the conversion of pyruvate and glyceraldehyde 3-phosphate (G-3-P) to 1-deoxyxylulose 5-phosphate (DXP). Prior art assays for DXPS activity have measured the amount of $[C^{14}]$-DXP produced in a reaction using $[C^{14}]$-labeled substrate. DXP concentration was then determined by HPLC or TLC analysis $[C^{14}]$-DXP. Such assays are not suitable for high throughput screening assays for DXPS activity.

In contrast to the prior art assays, the invention provides assays for DXPS activity based on a determination of the amount of substrate (pyruvate and/or G-3-P) remaining after a DXPS reaction. Surprisingly, we found that DXPS reacts with pyruvate in the absence of glyceraldehyde 3-phosphate. While no DXP is produced in this reaction, the concentration of pyruvate is depleted.

Thus, in one aspect, the invention provides a method for determining DXPS activity, comprising:
  a) contacting pyruvate and optionally, glyceraldehyde 3-phosphate, with a deoxyxylulose 5-phosphate synthase; and
  b) determining the concentration of pyruvate and/or glyceraldehyde 3-phosphate remaining after the contact in step (a).

The concentration of pyruvate and/or glyceraldehyde 3-phosphate remaining after this contact is inversely related to DXPS activity.

By deoxyxylulose 5-phosphate synthase (DXPS) is meant any enzyme that catalyzes the conversion of pyruvate and glyceraldehyde 3-phosphate to deoxyxylulose 5-phosphate. The DXPS may be a naturally occuring DXPS enzyme from any organism, an enzymatically active fragment of a naturally occuring DXPS enzyme, or a variant of a naturally occurring DXPS enzyme. Preferably, the DXPS is a plant DXPS or a prokaryotic DXPS. By plant DXPS is meant any DXPS enzyme that naturally occurs in at least one plant. Preferred plant DXPS enzymes include *Arabidopsis thaliana* DXPS, tDXPS (SEQ ID NO:2) and trxA/tDXPS (SEQ ID NO:3). By procaryotic DXPS is meant any DXPS enzyme that naturally occurs in at least one procaryote. Preferred procaryotic DXPS enzymes are from *Hemophilus influenzae, Rhodobacter capsulatus,* Synechocystus sp. PCC683, *Bacillus subtilis, Helicobacter pylori* and *Mycoplasma tuberculosis.*

As used herein, "enzymatically active fragments of a naturally occuring DXPS" refer to a polypeptide comprising at least 30 consecutive amino acids of the naturally occuring DXPS polypeptide and capable of catalyzing the conversion of pyruvate and glyceraldehyde 3-phosphate to DXP with at least 10% or more of the efficiency of the Arabidopsis tDXPS polypeptide represented as SEQ ID NO:2. The catalytic activity of any DXPS enzyme, fragment or variant thereof can be determined according to the method described in Example 5 below.

As used herein, "variant of a naturally occurring DXPS enzyme" refers to a polypeptide having at least 80% amino acid similarity with a naturally occuring DXPS polypeptide and capable of catalyzing the conversion of pyruvate and glyceraldehyde 3-phosphate to DXP with at least 10% or more of the efficiency of the Arabidopsis tDXPS polypeptide represented as SEQ ID NO:2.

Amino acid sequence similarity refers to amino acid residue positions in polypeptides that differ by conservative amino acid substitutions. An amino acid substitution is conservative if the substituted amino acid residue has similar chemical properties (e.g. charge or hydrophobicity) to the reference amino acid residue and therefore does not substantially change the functional properties of the polypeptide. In general, a substitution of an amino acid for another amino acid having the same type of R group is considered a conservative substitution. Amino acids can be classified into the following R groups: nonpolar, aliphatic; polar, uncharged; positively charged; negatively charged; and aromatic. Glycine, alanine, valine, leucine, isoleucine and proline have nonpolar aliphatic R groups. Serine, threonine, cysteine, methionine, asparagine and glutamine have polar uncharged R groups. Lysine, arginine and histidine have positively charged R groups. Aspartate and glutamate have negatively charged R groups. Phenylalanine, tyrosine and tryptophan have aromatic R groups.

The percent similarity between amino acid sequences can be determined using the "FASTA" similarity search algorithm of Pearson and Lipman (*Proc Natl Acad Sci USA* 85:2444, 1988) and Pearson (*Meth Enzymol* 183:63, 1990). Illustrative parameters for FASTA analysis are: ktup=1, gap opening penalty=10, gap extension penalty=1, and substitution matrix=1BLOSUM62. These parameters can be introduced into a FASTA program by modifying the scoring matrix file ("SMATRIX"), as explained in Appendix 2 of Pearson, 1990 (ibid.).

In the DXPS assays of the invention, pyruvate and optionally, glyceraldehyde 3-phosphate (G-3-P) are contacted with DXPS enzyme. Typically, the contact of pyruvate and G-3-P with DXPS will be made by combining these compounds in an aqueous solution that is compatible with DXPS activity.

Optimal buffer conditions, reagent concentrations, times and temperatures for the DXPS reaction can be determined by one skilled in the art. Preferably, the aqueous solution comprises 10–100 mM Tris pH 7.5; 5–100 $\mu$M pyruvate; 0–100 $\mu$M NADH; 1–50 mM DTT; 0.8–25 mM $MgCl_2$; and 0.08–5 mM ThDp. Most preferably, the aqueous solution comprises 50 mM Tris pH 7.5; 30 $\mu$M pyruvate; 25 $\mu$M NADH; 5 mM DTT; 2.5 mM $MgCl_2$; and 0.3 mM ThDp. If G-3-P is present, preferably the concentration is 5–200 $\mu$M and most preferably about 25 $\mu$M. The amount of DXPS protein will depend on the purity and activity of the DXPS preparation. For Arabidopsis tDXPS prepared as described in Example 2, the preferred amount is 500–1000 ng/50 $\mu$l reaction. Preferably, the DXPS reaction is conducted at approximately 37° C. and allowed to proceed for 30 minutes to three hours.

Following the contact of DXPS with pyruvate and optionally, G-3-P, the concentration of one or more DXPS substrate remaining is determined. It will be understood that the DXPS reaction need not proceed to completion prior to determining the concentration of the remaining pyruvate or glyceraldehyde 3-phosphate.

In a preferred embodiment, the concentration of pyruvate remaining after the contact with DXPS is determined. Methods for measuring the concentration of pyruvate are known to those skilled in the art. For example, the concentration of pyruvate can be determined by HPLC, by a pyruvate kinase assay or through the use of the pyruvate diagnostic kit such as the one provided by Sigma. By HPLC is meant high performance liquid chromatography.

In addition, pyruvate is a substrate for other reactions. Most notable is the conversion of pyruvate by lactate dehydrogenase (LDH; E.C. 1.1.1.27) in the presence of NADH to yield lactate and NAD. In a preferred embodiment, the concentration of pyruvate is determined by contacting the remaining pyruvate with lactate dehydrogenase and NADH and then determining the concentration of NADH. By NADH is meant $\beta$-nicotinamide adenine dinucleotide, reduced form. By NAD is meant $\beta$-nicotinamide adenine dinucleotide. The structures of NAD and NADH are described in Lehninger et al. Principles of Biochemistry, $2^{nd}$ Ed. Worth Publishers, New York, 1993.

Typically, the contact of pyruvate with NADH and LDH will be made by combining these compounds in an aqueous solution that is compatible with LDH activity. Optimal buffer conditions, reagent concentrations, times and temperatures for the LDH reaction can be determined by one skilled in the art. Preferably, the aqueous solution comprises 10–100 mM Tris pH 7.5; 1–100 $\mu$M NADH; 1–100 $\mu$M pyruvate and 0.2–10 units/ml LDH. Most preferably, the aqueous solution comprises 50 mM Tris pH 7.5, 25 $\mu$M NADH; 30 $\mu$M pyruvate and 2.5 units/ml LDH. Preferably, the LDH reaction is conducted at approximately room temperature and allowed to proceed for 1–10 minutes.

Following the contact of pyruvate and NADH with LDH, the concentration of NADH remaining can be determined. It will be understood that the LDH reaction need not proceed to completion prior to determining the concentration of the remaining NADH.

Methods for determining NADH concentration are known to those skilled in the art. Such methods include measurements of fluorescence and optical absorption. In one method, the concentration of NADH is determined by measuring the absorbance of NADH at approximately 320–360 nm, and preferably, at approximately 340 nm. More preferably, the concentration of NADH is determined by measuring the fluorescence of NADH at 340 nm excitation/460 nm emission.

As an alternative to determining the concentration of NADH, the concentration of NAD produced by contacting pyruvate with lactate dehydrogenase and NADH can be determined by measuring the absorbance of NAD at approximately 250–270 nm, and preferably at approximately 260 nm.

As an alternative to determining the concentration of pyruvate remaining after a DXPS reaction, the concentration of G-3-P remaining after this reaction can be determined. G-3-P can be measured by methods known to those skilled in the art, such as HPLC. In addition, G-3-P, like pyruvate, is a substrate for other reactions. For example, glyceraldehyde 3-phosphate and NAD are converted to 3-phosphoglycerate and NADH by glyceraldehyde 3-phosphate dehydrogenase (GAPH). Accordingly, following a glyceraldehyde 3-phosphate dehydrogenase reaction, the amount of NADH formed could be determined according to the methods described above.

The methods of the invention are particularly useful for identifying compounds that modulate DXPS activity. Such compounds are useful for the regulation of plant growth and development. For example, compounds that inhibit plant DXPS activity can be used as herbicides. Compounds that enhance DXPS activity can be used to increase production of thiamin (vitamin B1), pyridoxyl (vitamin B6) and isoprenoids in plants and other organisms.

Thus, the invention provides a method for identifying modulators of DXPS activity, comprising:

a) contacting pyruvate and optionally, glyceraldehyde 3-phosphate, with a deoxyxylulose 5-phosphate synthase, in the presence and the absence of at least one candidate compound; and b) comparing the concentration of pyruvate and/or glyceraldehyde 3-phosphate remaining after said contact in the absence of said candidate compound to said concentration in the presence of said candidate compound.

An increase in the concentration of pyruvate or glyceraldehyde 3-phosphate in the presence of the candidate compound would indicate that the candidate compound is an inhibitor of DXPS activity. A decrease in the concentration of pyruvate or glyceraldehyde 3-phosphate in the presence of the candidate compound would indicate that the candidate compound is an enhancer of DXPS activity.

EXPERIMENTAL

EXAMPLE 1

Cloning of A. thaliana DXPS cDNA and Expression in E. coli

The full-length cDNA for DXPS from A. thaliana was cloned using RT-PCR and inserted into a variety of expression vectors. Expression of the full length DXPS protein using baculovirus and E. coli expression systems failed to yield soluble protein. Similarly, expression of DXPS in E. coli as chimeric fusion proteins utilizing either N-terminal or C-terminal HIS-tag fusions or a thioredoxin fusion resulted in the association of recombinant DXPS with the insoluble fraction of the cell.

Our analysis of the full-length DXPS cDNA suggested that the first 58 amino acids encoded by this cDNA correspond to a plastid targeting sequence. In contrast, the prior art has predicted a 66 amino acid targeting sequence for Arabidopsis DXPS (Sprenger et al. (1997) *Proc Natl Acad Sci* 94:12857–12862). Utilizing RT-PCR on total RNA isolated from 14 day old *Arabidopsis thaliana* seedlings, we obtained a cDNA sequence for a truncated version of DXPS with the putative 58 amino acid targeting sequence removed (tDXPS). The truncated cDNA encoding tDXPS was ligated into the E. coli. expression vector pET32 (Novagen, Inc.). This expression vector allows for the expression of recombinant protein as a fusion product with thioredoxin (trxA). The expression vector also contains both a S-tag and a HIS sequence for purification by affinity or nickel chromatography, respectively, and both a thrombin protease cleavage site and an enterokinase (EK) protease cleavage site for removal of the Trx portion of the fusion protein (FIG. 2). Expression of the thioredoxin/tDXPS fusion protein in E. coli yielded quantities of soluble, active protein sufficient for the development of a high throughput screening (HTS) assay.

EXAMPLE 2

Purification of tDXPS pET32/tDXPS was transformed into *E. coli* AD494(DE3) lysS (Novagen), following the manufacturer's instructions. Transformed bacteria were grown in LB liquid media at 37° C. to an optical density of ~0.6 at 600 nm. At that point, isopropylthio-beta-galactoside (IPTG) was added to a final concentration of 1 mM and the culture was incubated at 37° C. for 4 additional hours. Bacteria were pelleted via centrifugation.

An *E. coli* pellet from 500 ml of an induced culture was lysed using BugBuster Bacteria Lysis Solution (Novagen) following the recommended protocol with the following modification. 20 µl of benzonase was used in the lysis step to help remove the DNA quickly from the cell lysate. This resulted in more complete lysis and reduced the viscosity of the mixture. The cell lysate was then clarified by centrifugation at 15,000×g for 10 minutes.

A volume of Ni-agarose beads sufficient to form a 5 ml column bed volume was equilibrated by washing twice with a 5×volume of Column Buffer (50 mM Tris, pH 7.5, 150 mM NaCl, 2.5 mM $MgCl_2$, 1 mM thiamin diphosphate (ThDp), 1 mM 2-mercaptoethanol). The supernate from the centrifuged cell lysate was then added to the equilibrated Ni-agarose beads. The supernate/Ni-agarose mixture was incubated on ice for approximately 20 minutes, with occasional mixing to keep the beads in suspension.

The supernate/Ni-agarose mixture was then poured into a column and the supernate was allowed to flow through. The column was washed with 50 ml of Wash Buffer (50 mM Tris, pH 7.5, 300 mM NaCl, 2.5 mM $MgCl_2$, 1 mM ThDp, 1 mM 2-mercaptoethanol, 20 mM imidazol).

Bound protein was eluted with Elution Buffer (50 mM Tris, pH 7.5, 150 mM NaCl, 500 mM imidazol, 2.5 mM $MgCl_2$, 1 mM ThDp, 1 mM 2-mercaptoethanol). Fractions containing protein as determined by a Bio-Rad™ protein assay were pooled, and concentrated to ~50% of the original volume using a 30,000 molecular weight cutoff spin filter.

Figure 3:
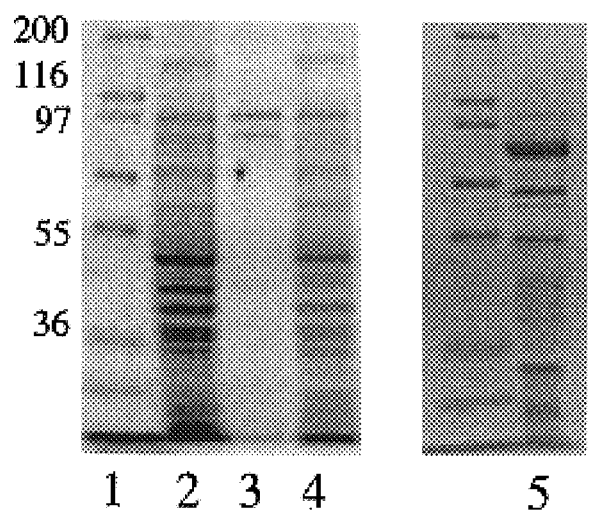
FIG. 3. Coomassie stained SDS-page gel of tDXPS purification. Lane 1) Molecular weight markers as indicated, lane 2) Clarified *E. coli* supernate, lane 3) Resuspended insoluble pellet, lane 4) Column flow-through, lane 5) Purified tDXPS.

Because of potential imidazole interference in detection of NADH fluorescence, pooled protein was then dialyzed (1:500) against Dialysis Buffer (50 mM Tris, pH 7.5, 150 mM NaCl, 2.5 mM $MgCl_2$, 1 mM ThDp, 5 mM DTT) twice, for 1 hour each time, at 4° C. A Pierce "Slide-a-lyser" cassette with a 10,000 molecular weight cutoff membrane was used for the dialysis. Purification was monitored by SDS-PAGE (FIG. 3). Typically, tDXPS is the major protein band comprising ~50% of the total protein in the purified sample.

The final protein concentration was determined using a BioRad protein assay kit. The protein was then flash-frozen and stored at −80° C. From a 500 ml *E. coli* culture (~1.1 grams) we routinely obtain ~2–2.5 mg of purified protein, or ~0.2% of the total cell pellet weight. When this protocol was scaled up for purification of a 5 liter *E. coli* culture, using a 10 ml Ni-agarose column, ~23 mg of protein were obtained.

Purified trxA/tDXPS was treated with 10 units of thrombin/mg of protein for 30 minutes at room temperature to remove the thioredoxin portion of the fusion protein. However subsequent experiments showed that no difference in activity of the trxA/tDXPS chimera as compared to tDXPS.

EXAMPLE 3

LC/MS Analysis of DXPS Activity of trxA/tDXPS

Approximately 100 ng of the trxA/tDXPS protein prepared according to the method described in Example 2 was assayed overnight in 50 mM Tris, pH 7.5, 3 mM $MgCl_2$, 1 mM ThDp, 1 mM DTT, 1 mM pyruvate, 3 mM G-3-P, at 37° C. 100 $\mu$l of this reaction mix was reserved for determination of the pyruvate concentration as described in Example 4 below. The reaction was terminated in the remaining reaction mix by heating to 80° C. for two minutes. The mixture was then centrifuged @ 15,000×g to remove the protein. LC/MS analysis of the supernatant showed that in the presence of the trxA/tDXPS protein, DXP was produced while pyruvate and G-3-P were depleted.

EXAMPLE 4

Analysis of DXPS Activity By Determination of Pyruvate Concentration Using a Lactate Dehydrogenase Assay We discovered that DXPS activity can be assessed by monitoring the disappearance of the substrate pyruvate. Pyruvate concentration can be determined indirectly by analysis of the conversion of pyruvate and NADH to lactic acid and NAD in the presence of lactate dehydrogenase. This second reaction can be monitored as a decrease in NADH concentration as the reaction proceeds. The concentration of NADH can be determined by measuring either the optical density of NADH at 340 nm or the relative fluorescence of NADH at 340 nm excitation/460 nm emission.

Figure 4:
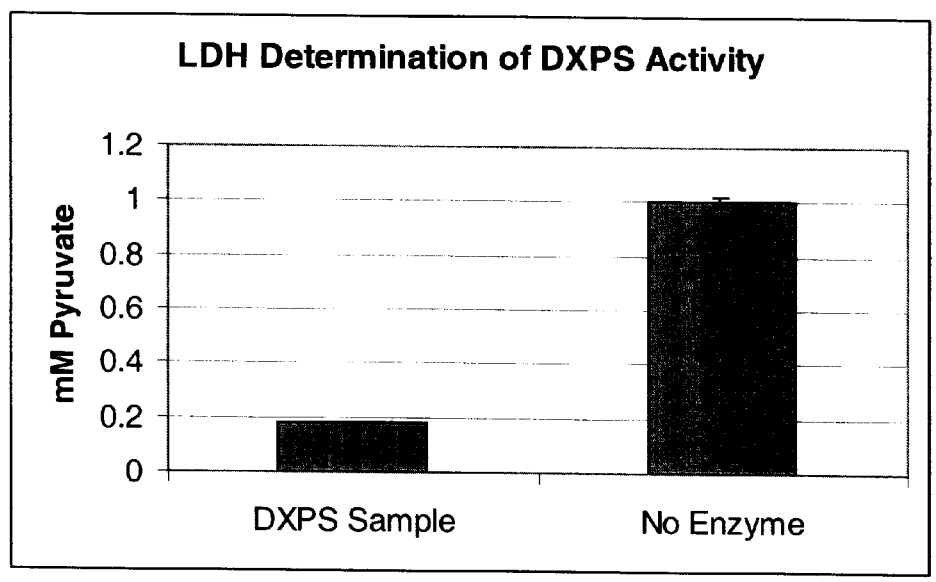
FIG. 4. Effect of DXPS enzyme on pyruvate concentration as determined by the conversion of NADH to NAD in the presence of pyruvate and lactate dehydrogenase (LDH).

In the first assay, absorbance of NADH was measured. Briefly, 100 $\mu$l of reaction mix reserved in Example 3 were mixed with 100 $\mu$l of 50 mM Tris pH 7.5, 0.5 units/ml lactate dehydrogenase (LDH), 1 mM NADH, and incubated at room temperature for 10 minutes. Optical density of NADH was determined at 340 nm for the assay samples and a pyruvate standard curve. The pyruvate concentrations from the assay mixtures are shown in FIG. 4. Pyruvate was depleted from the reaction containing recombinant tDXPS. Values are the mean of triplicate determinations, standard deviation is indicated.

Figure 5:
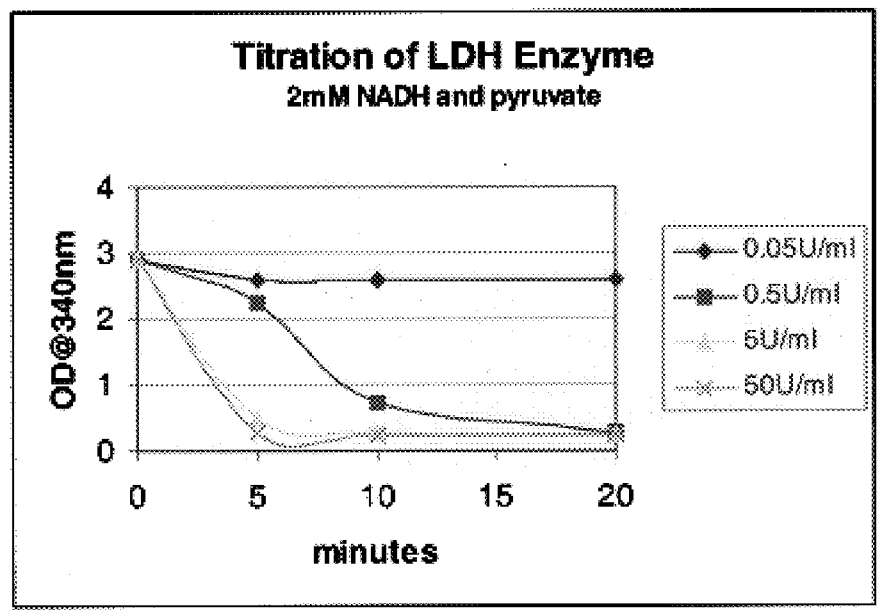
FIG. 5. Rate of conversion of pyruvate and NADH to lactic acid and NAD by lactate dehydrogenase.

The optimal concentration of LDH concentration per pyruvate assay was determined as follows. 2 mM pyruvate and 2 mM NADH were mixed with an equal volume of LDH in Tris buffer. Absorbance at 340 nm was then determined at 0, 5, 10 and 20 minutes. The results are shown in FIG. 5. Values are the mean of duplicate determinations. Using 5 units/ml or more of LDH and adding in equal volumes to the reaction mix, the conversion of pyruvate to lactic acid and NAD is essentially completed in 5 minutes at room temperature at 2 mM NADH and pyruvate.

Figure 6:
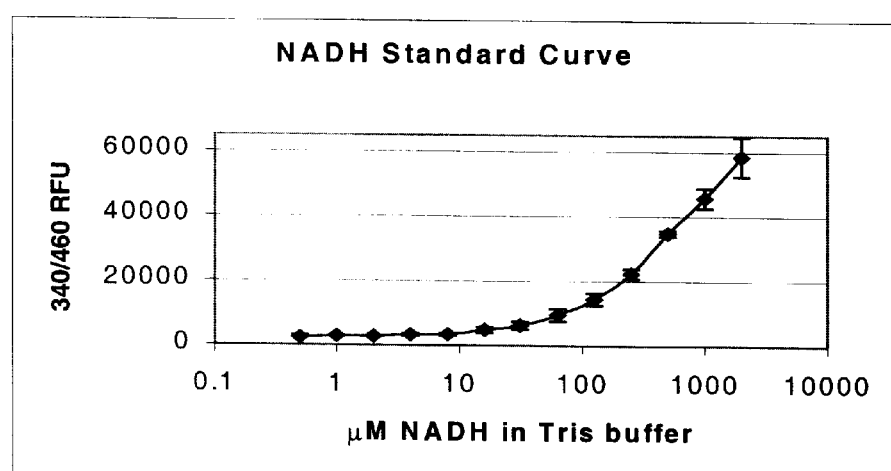
FIG. 6. Standard curve of NADH concentration using 340 nm excitation/460 nm emission fluorescence of NADH.

In the second assay, the concentration of NADH was determined by fluorescence. As a first step, a standard curve for NADH fluorescence was determined using 340 nm excitation/460 nm emission fluorescence. 50 $\mu$l/well of NADH solution was titrated in a 384 well plate and the relative fluorescence units (RFU) were determined. The automatic gain adjustment was used to set the gain level in the well with the highest concentration of NADH to give them a reading that was approximately 90% of the maximum value that the machine could determine. The results are shown in FIG. 6. Values are the mean of triplicate determinations. Standard deviation is shown as error.

Figure 7:
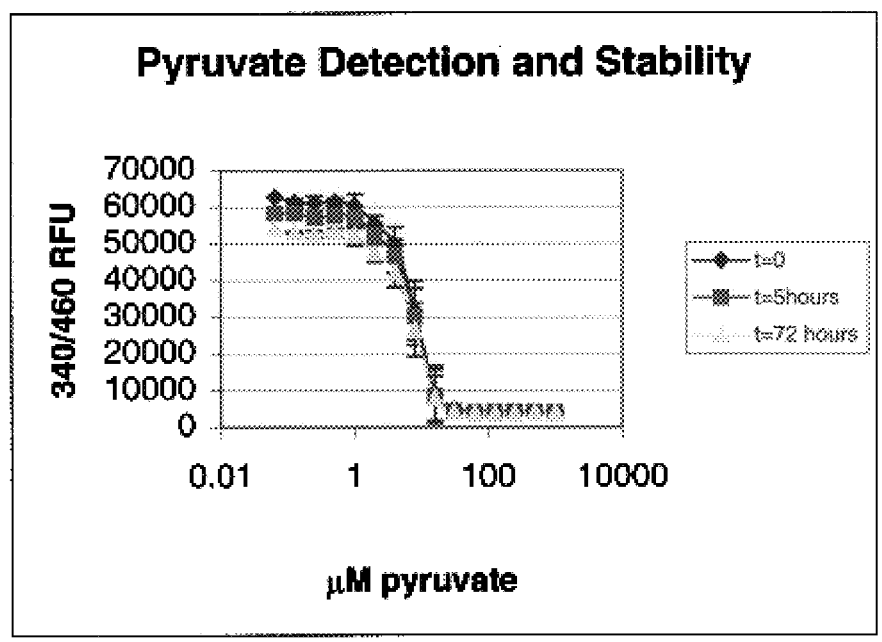
FIG. 7. Standard curve of pyruvate concentration by fluorescence of NADH following a lactate dehydrogenase reaction. The relative fluorescence of NADH at 340 nm excitation–460 nm emission is shown.
Figure 8:
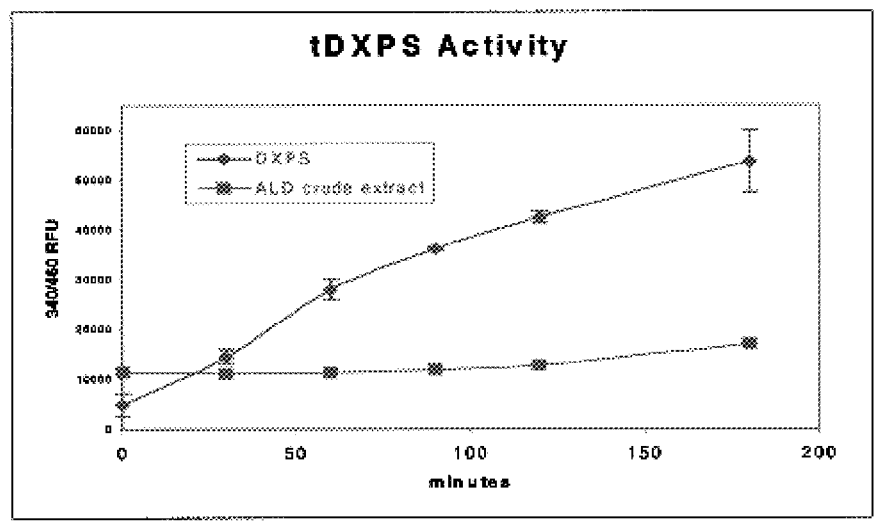
FIG. 8. Determination of reaction time for tDXPS as measured by NADH fluorescence in a lactate dehydrogenase reaction. ♦-DXPS, ■-*E. coli* crude extract.
Figure 9:
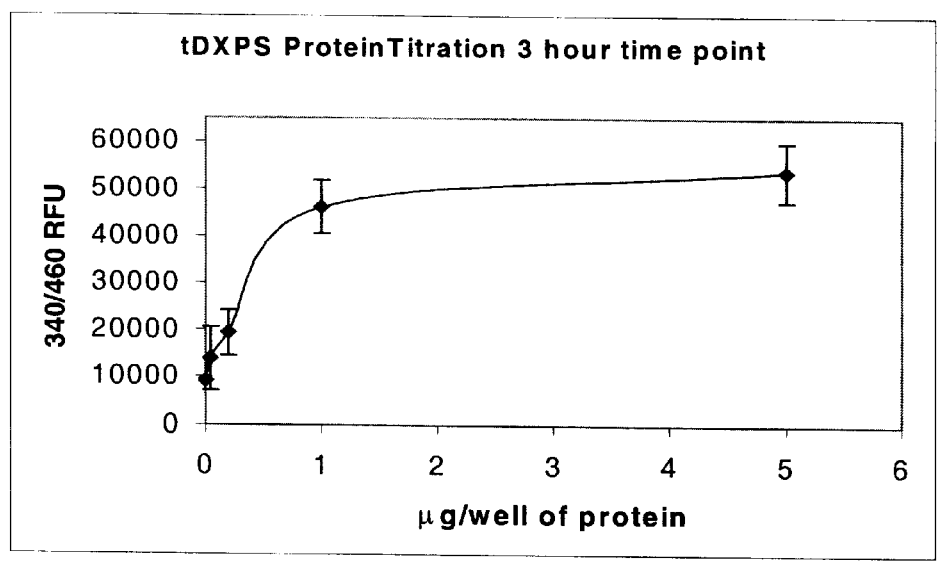
FIG. 9. Total Activity at a 3-hour time point for various amounts of tDXPS protein. Values are the mean of triplicate determinations, with standard deviation indicated. 1 µg/well of protein was chosen for all further experiments.

As a second step, a standard curve for pyruvate concentration was determined using detection of NADH fluorescence in the LDH assay. Detection buffer (50 mM Tris, pH 7.5, 5 units/ml of LDH, 25 $\mu$M NADH) was added to equal volumes of buffer containing various amounts of pyruvate. The relative fluorescence units (RFU) for NADH were determined at 340 nm excitation–460 nm emission in a solid white, Greiner 384 well plate. The detection buffer was made fresh for each time point, the pyruvate solution was added to the plate at 0 hours and the plate was incubated at room temperature until assayed for each time point. The results are shown in FIG. 7. Pyruvate shows good stability at room temperature and the detection of pyruvate concentration shows excellent repeatability. Values are the mean of triplicate determinations, standard deviation is indicated as error.

trxA/tDXPS activity was determined by fluorescence as follows. DXPS reactions were performed in a 384 well plate using 5$\mu$g/well of protein, or crude *E. coli* supernate that does not contain the DNA for recombinant DXPS. The reaction mixture contained 50 mM Tris, pH 7.5, 50 $\mu$M glyceraldehyde 3-phosphate (G-3-P), 25 $\mu$M pyruvate, 25 mM DTT, 10 mM $MgCl_2$, and 1 mM thiamin diphosphate (ThDp). Reactions were performed at 37° C. in 50 $\mu$l, and were terminated with the addition of an equal volume of a 50 mM Tris (pH7.5) solution containing 5 units/ml lactate dehydrogenase and 25 $\mu$M NADH. The results are shown in FIG. 8. Values indicated for DXPS are the mean of triplicate determinations, with the error bars showing standard deviation, values for the crude supernate are single point determinations. This experiment was also done in a 96 well plate with similar results. Titration of tDXPS protein at a three hour time point showed that 1 ug/well of the purified tDXPS protein gave good activity in this assay (FIG. 9).

The thioredoxin/tDXPS fusion protein was cleaved with biotinylated thrombin at room temperature for 30 minutes, then assayed for DXPS activity. Activity was compared to an equal amount (1 $\mu$g/well) of unclipped protein (control). Removal of the thioredoxin portion of the fusion did not increase enzymatic activity of the protein as compared to protein that retained the thioredoxin tag.

EXAMPLE 5

Optimization of DXPS Assay

The concentrations of thioredoxin/tDXPS fusion protein, glyceraldehyde 3-phosphate, DTT, $MgCl_2$, ThDp, pyruvate, NADH and LDH were individually titrated in order to determine the optimal conditions for the assay of DXPS activity. The conditions and protocols chosen for high throughput screening of DXPS activity are as follows:

2×Assay Buffer:
  50 mM Tris, pH7.5
  50 $\mu$M DL-glyceraldehyde 3-phosphate
  60 $\mu$M pyruvate
  50 $\mu$M NADH
  5 mM DTT
  2.5 mM $MgCl_2$
  0.3 mM ThDp
Protein Dilution Buffer:
  50 mM Tris, pH7.5
  5 mM DTT 2.5 mM MgCl$_2$ 0.3 mM ThDp Final Concentrations in the Assay:

50 mM Tris pH 7.5

25 μM DL-glyceraldehyde 3-phosphate

30 μM pyruvate

25 μM NADH 5 mM DTT 2.5 mM MgCl$_2$ 0.3 mM ThDp

Detection Buffer:

50 mM Tris, pH 7.5

5 units/ml LDH

Assay Protocol

*All buffers need to be maintained @4° C. on the robot deck

1) Add 25 μl/well of 2×assay buffer by multidrop.

2) Add 5 μl/well of a test compound

3) Add 20 μl/well of protein (1 μg/well total protein) by multidrop

4) Incubate for three hours @ 37° C.

5) Add 50 μl/well of LDH detection buffer

6) Read fluorescence @ 340em.–460ex.

Assay plate:

Greiner solid white 384 well plate

Reagent List:

DL-glyceraldehyde 3-phosphate Sigma Cat.#G 5251

Pyruvate, sodium salt Sigma Cat #P 2256

NADH, reduced form Sigma Cat #N 8129

LDH Sigma Cat #L 2500 One unit will reduce 1.0 μmol of pyruvate to lactate per minute at pH 7.5 at 37° C.

ThDp (cocarboxylase) Sigma Cat #C 8754

MgCl$_2$ Sigma Cat # M 8266

DTT Sigma Cat #D 5545

384 well Statistical Analysis:

50 μl of assay buffer plus 50 μl of detection buffer were added to a 384 well Greiner, solid white plate by multidrop. NADH concentration was then determined by fluorescence as described in the above protocol.

EXAMPLE 6

G-3-P is Not Necessary for the Assay of DXPS Activity

Even though a Km value could be determined for G-3-P, it was noted that there was still a significant difference between the no enzyme control and the no G-3-P control. To try and determine the reason for this, a DXPS reaction (1 mM pyruvate, +/−1 mM G-3-P, standard concentrations for the remaining assay components, 500 μl total volume, 10 μg tDXPS/reaction) was prepared and allowed to incubate overnight at 37° C. The reactions were terminated by heating the samples at 90° C. for two minutes. The samples were centrifuged at 15,000 rpm for 10 minutes to remove the precipitated protein, then analyzed by LC/MS. In the absence of enzyme, pyruvate could be detected. In the presence of enzyme and G-3-P, the appearance of DXP product was accompanied by the loss of pyruvate. However, in the presence of enzyme and absence of G-3-P, the pyruvate peak was lost without the concomitant formation of DXP. This shows the ability of DXPS to complete the first step in the DXP synthesis reaction in the absence of G-3-P.

Figure 10:
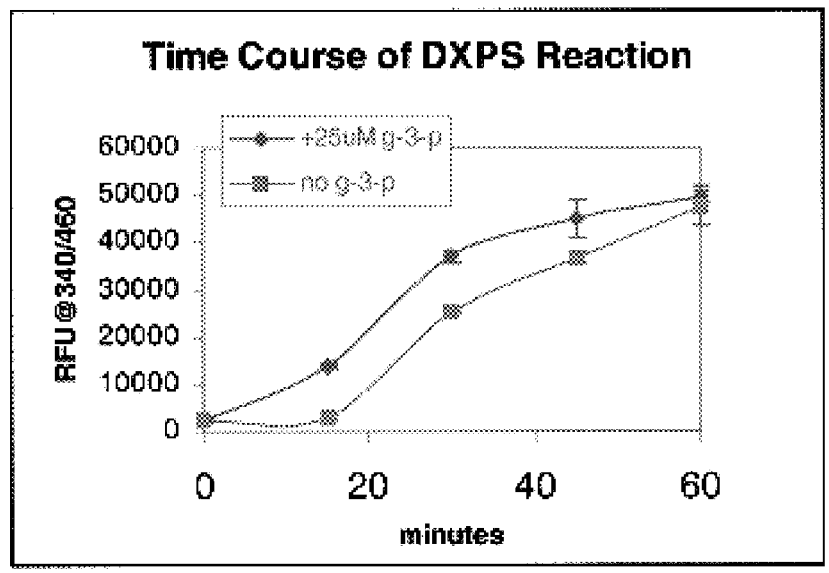
FIG. 10. Time course of DXPS reaction in the presence and absence of glyceraldehyde 3-phosphate (g-3-p).

The rate of the DXPS reaction was compared in the presence and absence of G-3-P. 1 μg DXPS was mixed with 30 μM pyruvate, 50 mM Tris pH 7.5, 25 μM NADH, 5 mM DTT, 2.5 mM MgCl$_2$, 0.3 mM ThDp and in the presence or absence of 25 mM G-3-P. The reaction was incubated at 37° C. for 15, 30 or 60 minutes and then terminated by the addition of detection buffer (50 mM Tris, pH 7.5, 5 units/ml LDH). Fluorescence was measured at 340/460. The results are shown in FIG. 10. Again, even in the absence of G-3-P, the enzyme is capable of utilizing pyruvate as a substrate. Although the rate of the reaction is slower, the reaction can still go to completion. All values are in triplicate, standard deviation is indicated.

While the foregoing describes certain embodiments of the invention, it will be understood by those skilled in the art that variations and modifications may be made and still fall within the scope of the invention.

What is claimed is:

1. A method for determining deoxyxylulose 5-phosphate synthase activity, comprising:
   a) contacting pyruvate and optionally, glyceraldehyde 3-phosphate, with the polypeptide of SEQ ID NO:2 or SEQ ID NO:3; and
   b) determining the concentration of pyruvate and/or glyceradehyde 3-phosphate remaining after the contact in step (a).

2. The method of claim 1, wherein said optional glyceraldehyde 3-phosphate is omitted.

3. The method of claim 1, wherein said polypeptide is the polypeptide of SEQ ID NO:2.

4. The method of claim 1, wherein said polypeptide is the polypeptide of SEQ ID NO:3.

5. The method of claim 1, wherein the concentration of pyruvate is determined.

6. The method of claim 5, wherein the concentration of pyruvate is determined by HPLC.

7. The method of claim 5, wherein the concentration of pyruvate is determined by contacting said pyruvate with lactate dehydrogenase and NADH and then determining the concentration of NADH.

8. The method of claim 7, wherein the concentration of NADH is determined by measuring the fluorescence of said NADH.

9. The method of claim 7, wherein the concentration of NADH is determined by measuring the absorbance of NADH.

10. A method for determining deoxyxylulose 5-phosphate synthase activity, comprising:
    a) contacting pyruvate with a deoxyxylulose 5-phosphate synthase of SEQ ID NO:1, 2 or 3, wherein said contacting is in the absence of glyceraldehyde 3-phosphate; and
    b) determining the concentration of pyruvate remaining after the contact in step (a).

11. The method of claim 10, wherein said deoxyxylulose 5-phosphate synthase is the polypeptide of SEQ ID NO:1.

12. The method of claim 10, wherein said deoxyxylulose 5-pbosphate synthase is the polypeptide of SEQ ID NO:2.

13. The method of claim 10, wherein said deoxyxylulose 5-phosphate synthase is the polypeptide of SEQ ID NO:3.

14. The method of claim 10, wherein the concentration of pyruvate is determined by HPLC.

15. The method of claim 10, wherein the concentration of pyruvate is determined by contacting said pyruvate with lactate dehydrogenase and NADH and then determining the concentration of NADH.

16. The method of claim 15, wherein the concentration of NADH is determined by measuring the fluorescence of said NADH.

17. The method of claim 15, wherein the concentration of NADH is determined by measuring the absorbance of NADH.

* * * * *